(12) United States Patent
Ashby et al.

(10) Patent No.: US 7,955,353 B1
(45) Date of Patent: *Jun. 7, 2011

(54) DISSOLVABLE CLOSURE DEVICE

(75) Inventors: Mark Ashby, Launa Niguel, CA (US); Eduardo Chi Sing, Dana Point, CA (US); Tin T. Tran, Anaheim, CA (US)

(73) Assignee: Sub-Q, Inc., San Clemente, CA (US)

( * ) Notice: Subject to any disclaimer, the term of this patent is extended or adjusted under 35 U.S.C. 154(b) by 2358 days.

This patent is subject to a terminal disclaimer.

(21) Appl. No.: 10/461,587

(22) Filed: Jun. 12, 2003

Related U.S. Application Data (63) Continuation-in-part of application No. 10/287,922, filed on Nov. 4, 2002, now Pat. No. 7,455,680.

(51) Int. Cl.
*A61B 17/08* (2006.01)
*A61D 1/00* (2006.01)
(52) U.S. Cl. .................................. 606/213; 606/108
(58) Field of Classification Search .............. 606/213, 606/214, 108, 216
See application file for complete search history.

(56) References Cited

U.S. PATENT DOCUMENTS

| | | |
|---|---|---|
| 581,235 A | 4/1897 | Kenyon |
| 1,578,517 A | 3/1926 | Hein |
| 2,086,580 A | 7/1937 | Shirley |
| 2,492,458 A | 12/1946 | Bering, Jr. |
| 2,465,357 A | 3/1949 | Correll |
| 2,507,244 A | 5/1950 | Correll |
| 2,558,395 A | 6/1951 | Studer |
| 2,597,011 A | 5/1952 | MacMasters et al. |
| 2,680,442 A | 6/1954 | Linzmayer |
| 2,761,446 A | 9/1956 | Reed |
| 2,814,294 A | 11/1957 | Figge |
| 2,824,092 A | 2/1959 | Thompson |
| 2,899,362 A | 8/1959 | Sieger, Jr. et al. |
| 3,157,524 A | 11/1964 | Artandi |
| 3,724,465 A | 4/1973 | Duchane |
| 4,000,741 A | 1/1977 | Binard et al. |
| 4,077,409 A | 3/1978 | Murray et al. |
| 4,211,323 A | 7/1980 | Olsen |
| 4,218,155 A | 8/1980 | Weidner |

(Continued)

FOREIGN PATENT DOCUMENTS

EP 0032826 7/1981

(Continued)

OTHER PUBLICATIONS

Allison, D., et al., "Percutaneous liver biopsy and track embolization with steel coils", Radiology, vol. 169, pp. 261-263, (1998).

(Continued)

*Primary Examiner* — Todd E Manahan
*Assistant Examiner* — Michael G Mendoza
(74) *Attorney, Agent, or Firm* — Seager, Tufte & Wickhem LLC (57) ABSTRACT

The present invention provides for a method and apparatus to provide hemostasis at a puncture site having a communication tube with a lumen, a top and a bottom; a hemostatic material positioned around the communication tube bottom, the hemostatic material having a first end and a second end; and a hemostatic material cover positioned around the hemostatic material and the communication tube bottom, wherein the hemostatic material cover forms a hollow distal tip cavity at the hemostatic material first end.

27 Claims, 10 Drawing Sheets

U.S. PATENT DOCUMENTS

| | | |
|---|---|---|
| 4,238,480 A | 12/1980 | Sawyer |
| 4,292,972 A | 10/1981 | Pawelchak |
| 4,323,072 A | 4/1982 | Rosenbluth et al. |
| 4,340,066 A | 7/1982 | Shah |
| 4,390,018 A | 6/1983 | Zuloowski |
| 4,404,970 A | 9/1983 | Sawyer |
| 4,515,637 A | 5/1985 | Cioca |
| 4,587,969 A | 5/1986 | Gillis |
| 4,588,395 A | 5/1986 | Lemelson |
| 4,619,261 A | 10/1986 | Guerriero |
| 4,619,913 A | 10/1986 | Luck et al. |
| 4,645,488 A | 2/1987 | Matukas |
| 4,708,718 A | 11/1987 | Daniels |
| 4,744,364 A | 5/1988 | Kensey |
| 4,790,819 A | 12/1988 | Li et al. |
| 4,829,994 A | 5/1989 | Kurth |
| 4,850,960 A | 7/1989 | Grayzel |
| 4,852,568 A | 8/1989 | Kensey |
| 4,869,143 A | 9/1989 | Merrick |
| 4,890,612 A | 1/1990 | Kensey |
| 4,900,303 A | 2/1990 | Lemelson |
| 4,929,246 A | 5/1990 | Sinofaky |
| 4,936,835 A | 6/1990 | Haaga |
| 4,950,234 A | 8/1990 | Fujioka et al. |
| 5,007,895 A | 4/1991 | Burnett |
| 5,021,059 A | 6/1991 | Kensey et al. |
| 5,053,046 A | 10/1991 | Janese |
| 5,061,274 A | 10/1991 | Kensey |
| 5,080,655 A | 1/1992 | Haaga |
| 5,108,421 A | 4/1992 | Fowler |
| 5,163,904 A | 11/1992 | Lampropoulos et al. |
| 5,167,624 A | 12/1992 | Butler et al. |
| 5,192,300 A | 3/1993 | Fowler |
| 5,192,301 A | 3/1993 | Kamiya et al. |
| 5,195,988 A | 3/1993 | Haaga |
| 5,220,926 A | 6/1993 | Jones |
| 5,221,259 A | 6/1993 | Weldon et al. |
| 5,242,683 A | 9/1993 | Klaveness |
| 5,254,105 A * | 10/1993 | Haaga ................... 604/265 |
| 5,275,616 A | 1/1994 | Fowler |
| 5,282,827 A | 2/1994 | Kensey et al. |
| 5,290,310 A * | 3/1994 | Makower et al. ............ 606/213 |
| 5,310,407 A | 5/1994 | Casale |
| 5,322,515 A | 6/1994 | Karas et al. |
| 5,324,306 A | 6/1994 | Makower et al. |
| 5,325,857 A | 7/1994 | Nabai et al. |
| 5,334,216 A | 8/1994 | Vidal et al. |
| 5,366,480 A | 11/1994 | Corriveau et al. |
| 5,370,656 A | 12/1994 | Shevel |
| 5,383,896 A | 1/1995 | Gershony et al. |
| 5,383,899 A | 1/1995 | Hammersiag |
| 5,385,550 A | 1/1995 | Su et al. |
| 5,388,588 A | 2/1995 | Nabai et al. |
| 5,391,183 A | 2/1995 | Janzen et al. |
| 5,417,699 A | 5/1995 | Klein |
| 5,419,765 A | 5/1995 | Weldon et al. |
| 5,431,639 A | 7/1995 | Shaw |
| 5,437,292 A | 8/1995 | Kipshidze |
| 5,437,631 A | 8/1995 | Janzen |
| 5,443,481 A | 8/1995 | Lee |
| 5,467,780 A | 11/1995 | Nabai et al. |
| 5,478,352 A | 12/1995 | Fowler |
| 5,479,936 A | 1/1996 | Nabai et al. |
| 5,486,195 A | 1/1996 | Myers |
| 5,490,736 A | 2/1996 | Haber |
| 5,507,279 A | 4/1996 | Fortune |
| 5,522,840 A | 6/1996 | Krajicek |
| 5,522,850 A | 6/1996 | Yomtov et al. |
| 5,526,822 A | 6/1996 | Burbank et al. |
| 5,527,332 A | 6/1996 | Clement |
| 5,529,577 A | 6/1996 | Hammershiag |
| 5,540,715 A | 7/1996 | Katseros et al. |
| 5,542,914 A | 8/1996 | Van Iten |
| 5,545,178 A | 8/1996 | Kensey et al. |
| 5,554,108 A | 9/1996 | Browning et al. |
| 5,558,853 A | 9/1996 | Quay |
| 5,591,204 A | 1/1997 | Janzen et al. |
| 5,591,205 A | 1/1997 | Fowler |
| 5,601,602 A | 2/1997 | Fowler |
| 5,601,603 A | 2/1997 | Illi |
| 5,645,566 A | 7/1997 | Brennenman et al. |
| 5,649,547 A | 7/1997 | Ritchart et al. |
| 5,653,730 A | 8/1997 | Hammersiag |
| 5,665,107 A | 9/1997 | Hammersiag |
| 5,676,689 A | 10/1997 | Kensey |
| 5,681,279 A | 10/1997 | Roper et al. |
| 5,716,375 A | 2/1998 | Fowler |
| 5,725,498 A | 3/1998 | Janzen et al. |
| 5,741,223 A | 4/1998 | Janzen et al. |
| 5,769,086 A | 6/1998 | Ritchart et al. |
| 5,769,813 A | 6/1998 | Peiler et al. |
| 5,775,333 A | 7/1998 | Burbank et al. |
| 5,782,861 A | 7/1998 | Cragg et al. |
| 5,800,389 A | 9/1998 | Burney et al. |
| 5,810,806 A | 9/1998 | Ritchart et al. |
| 5,830,130 A | 11/1998 | Janzen et al. |
| 5,858,008 A | 1/1999 | Capaccio |
| 5,868,762 A | 2/1999 | Cragg et al. |
| 5,902,310 A | 5/1999 | Foerster et al. |
| 5,984,950 A | 11/1999 | Cragg et al. |
| 6,007,563 A | 12/1999 | Nash et al. |
| 6,027,471 A | 2/2000 | Fallon et al. |
| 6,027,482 A | 2/2000 | Imbert |
| 6,071,300 A | 6/2000 | Brenneman et al. |
| 6,071,301 A | 6/2000 | Cragg et al. |
| 6,086,607 A | 7/2000 | Cragg et al. |
| 6,161,034 A | 12/2000 | Burbank et al. |
| 6,162,192 A | 12/2000 | Cragg et al. |
| 6,183,497 B1 | 2/2001 | Sing et al. |
| 6,200,328 B1 | 3/2001 | Cragg et al. |
| 6,315,753 B1 | 11/2001 | Cragg et al. |
| 6,610,025 B2 | 8/2003 | Berg et al. |
| 6,984,219 B2 | 1/2006 | Ashby et al. |
| 7,156,880 B2 * | 1/2007 | Evans et al. ................. 623/23.51 |

FOREIGN PATENT DOCUMENTS

| | | |
|---|---|---|
| EP | 0476178 | 3/1992 |
| EP | 0482350 | 4/1992 |
| EP | 0557963 | 2/1993 |
| EP | 0637431 | 11/1994 |
| FR | 2641692 | 7/1990 |
| GB | 1509023 | 4/1978 |
| GB | 1569660 | 6/1980 |
| SU | 782814 | 11/1980 |
| SU | 1088709 A | 4/1984 |
| WO | WO 91/12847 | 9/1991 |
| WO | WO 94/02072 | 2/1994 |
| WO | WO 94/28800 | 12/1994 |
| WO | WO 95/28124 | 10/1995 |
| WO | WO 95/32669 | 12/1995 |
| WO | WO 95/32671 | 12/1995 |
| WO | WO 96/08208 | 3/1996 |
| WO | WO 96/24290 | 8/1996 |
| WO | WO 98/06346 | 2/1998 |
| WO | WO 99/66834 | 12/1999 |

OTHER PUBLICATIONS

J. Bryne Review Article: Endovascular treatments for intracranial anuerysms, 1996 The British journal of radiology; 98,891-899.

Chuang, V., et al., "Sheath needle for liver biopsy in high-risk patience", Radiology, vol. 166, pp. 261-262 (1988).

John T. Correll, et al., A new Physiologically absorbable sponge.

John T. Correll, et al. Biologic investigations of new absorbable sponge; p. 585.

Fandrich, C., et al. "Small guage gelfoam plug liver biopsy in high risk patients", Australian Radiology, vol. 40, pp. 230-234 (1996).

Foran, JPM, et al. "Early mobilisation after percutaneous cardiac catheterisation using collagen plug (vasoseal) maemostatis" BRHeart, vol. 69, pp. 424-429 (1993).

Gibbs, JSR, "Femoral arterial hemostasis" J. Interventional card, vol. 5, pp. 85-88 (1992).

Journal of interventional cardiology vol. 5 No. 2 June.

Kassell, et al. Size of Intracranial aneurysm; vol. 12, No. 3, (1983).

Kiemeneiji, F, et al., "Improved anticoagulation management after Palmaz Schatz coronary stent implantation by sealing the arterial puncture site with vascular hemostasis device", Catheterization and Cardiovascular diagnosis, vol. 30, pp. 1685-1692 (1995).

Kussmaul, WG, "Rapid arterial hemostasis", J. Am. Coll. Card., vol. 25, pp. 1685-1692 (1995).

Pharmacia & Upjohn manufacturer brochure gelfoam sterile sponge, sterile powder and sterile film, pp. 1-34 (May 1997).

Pharmacia & Upjohn manufacturer brochure "gelfoam sterile powder ", (Feb. 1996).

Pharmacia & Upjohn manufacturer brochure, "gelfoam sterile powder" (Mar. 1996).

Pharmacia & Upjohn manufacturer brochure (Sep. 1996).

Pharmacia & Upjohn manufacturer specification, "Gelfoam sterile sponge, sterile powder and sterile film" pp. 1-23 (Nov. 1996).

Riley, SA, Percutaneous liver biopsy with plugging of needle track: a safe method for use in patients with impaired coagulation, The lancet, p. 436 (1964).

Sanborn, T. Multicenter randomized trial comparing perutaneous collagen hemostasis device with conventional manual compression after diagnostic angiography and angioplasty, J. Am. Coll. Card., vol. 22, pp. 1273-1279, (1993).

Schievink, et al. The new england journal of medicaine; review articles; intracanial aneurysms; Jan. 2, 1997.

Scharader, R. "Collagen appl.", Catheterization & cardiovascular diagnosis (1992) pp. 298-302.

Silber, S., "Rapid hemostasis of arterial puncture sites with collagen in patients undergoing diagnostic interventional cardiac catherterization", clinical cardiology, vol. 20, pp. 981-992, (1997).

Smith, T., "Percutaneous transhepatic liver biopsy with tract embolization", Radiology, vol. 198, pp. 769-774 (1996).

Szikora, et al. Combined Use of stents and cells to treat experimental wide-necked carotid aneuryms: Preliminary results; AJNR AM newradiol 15: 1091-1102, Jun. 1994.

Szikora, et al. Endovascular treatment of experimental anuerysms with liquid polymers: vol. 38, No. 2, Feb. 1996.

Turjman, et al. Combined stent implantation & endosacular coil placement for tretment of experimental wide-necked aneurysms:AJNRAM J. Neuroradio 15: 1087-1090 Jun. 1994.

Yoshimoto, et al cerebral anuerysms unrelated to arterial bifurcations; Acta neurochir (Wien) (96) 138: 958-964.

Zins, M., "US-guided percutaneous liver biopsy with plugging of the needle track" radiology, vol. 187, pp. 841-843,(1992).

* cited by examiner

DISSOLVABLE CLOSURE DEVICE

CROSS-REFERENCE TO RELATED APPLICATIONS

This application is a continuation-in-part of, and claims priority under 35 U.S.C. §120 to, and incorporates by reference herein in their entirety: 1. U.S. patent application Ser. No. 10/287,922, filed Nov. 4, 2002 now U.S. Pat. No. 7,455,680, by inventors: Mark Ashby and Tin Tran, entitled "APPARATUS AND METHOD FOR INHIBITING BLOOD LOSS".

FIELD OF THE INVENTION

The present invention relates to providing hemostasis at a puncture site. More particularly, the present invention relates to providing hemostasis at a puncture site using a dissolvable closure device.

BACKGROUND OF THE INVENTION

A large number of diagnostic and interventional procedures involve the percutaneous introduction of instrumentation into a vein or artery. For example, coronary angioplasty, angiography, atherectomy, stenting of arteries, and many other procedures often involve accessing the vasculature through a catheter placed in the femoral artery or other, blood vessel. Once the procedure is completed and the catheter or other instrumentation is removed, bleeding from the punctured artery must be controlled.

Traditionally, external pressure is applied to the skin entry site to stem bleeding from a puncture wound in a blood vessel. Pressure is continued until hemostasis has occurred at the puncture site. In some instances, pressure must be applied for up to an hour or more during which time the patient is uncomfortably immobilized. In addition, a risk of hematoma exists since bleeding from the vessel may continue beneath the skin until sufficient clotting effects hemostasis. Further, external pressure to close the vascular puncture site works best when the vessel is close to the skin surface but may be unsuitable for patients with substantial amounts of subcutaneous adipose tissue since the skin surface may be a considerable distance from the vascular puncture site.

An approach to subcutaneous blood vessel puncture closure involves the delivery of non-absorbable tissue adhesives, such cyanoacrylate, to the perforation site. Such a system is disclosed in U.S. Pat. No. 5,383,899.

Another approach is the application of an absorbable material such as collagen or a non-absorbable tissue adhesive at the puncture site. However, the disadvantages of this application includes: 1) possible injection of the material into the blood vessel causing thrombosis; and, 2) the inability to accurately place the absorbable material plug directly over the puncture site.

The use of an anchor and plug system addresses these problems to some extent but provides other problems including: 1) complex and difficult application; 2) partial occlusion of the blood vessel by the anchor when placed properly; and 3) complete blockage of the blood vessel or a branch of the blood vessel by the anchor if placed improperly. Another problem with the anchor and plug system involves reaccess. Reaccess of a particular blood vessel site sealed with an anchor and plug system is not possible until the anchor has been completely absorbed because the anchor could be dislodged into the blood stream by an attempt to reaccess.

Thus, there is still a need for an apparatus and method to accurately, efficiently and easily locate the blood vessel puncture site and provide hemostasis at the puncture site.

BRIEF DESCRIPTION OF THE INVENTION

The present invention provides for a method and apparatus to provide hemostasis at a puncture site having a communication tube with a lumen, a top and a bottom; a hemostatic material positioned around the communication tube bottom, the hemostatic material having a first end and a second end; and a hemostatic material cover positioned around the hemostatic material and the communication tube bottom, wherein the hemostatic material cover forms a hollow distal tip cavity at the hemostatic material first end.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

In the drawings.

DETAILED DESCRIPTION

Embodiments of the present invention are described herein in the context of a dissolvable closure device. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure Precisely locating a blood vessel and providing hemostasis at the blood vessel puncture site is important for procedures such as puncture closure. Thus, the present invention is directed to a method and apparatus that accurately, efficiently, and easily provides hemostasis at the blood vessel puncture site.

Figure 1:
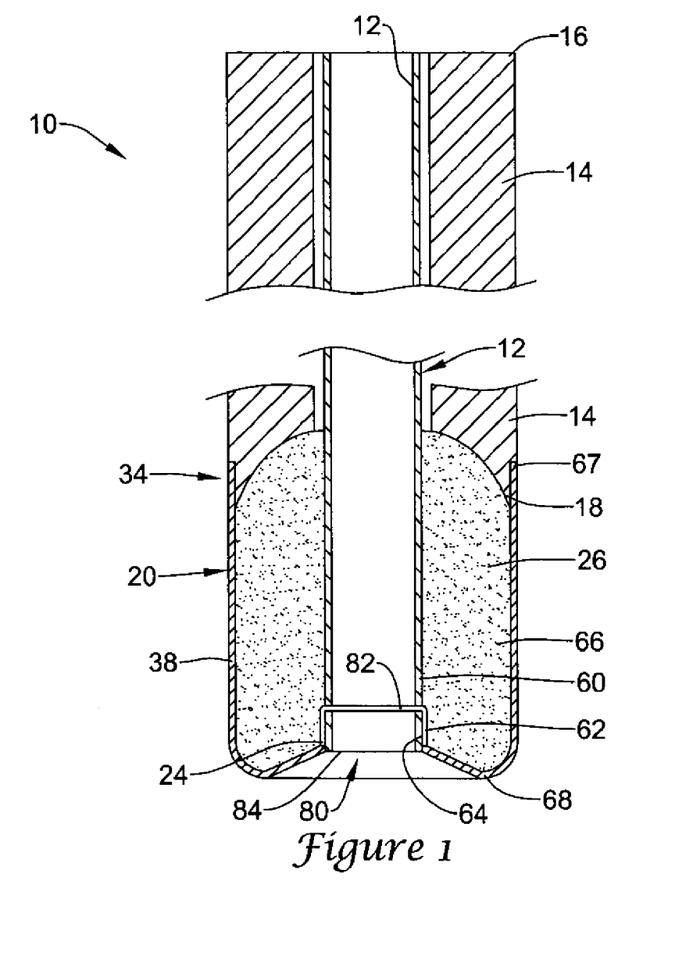
FIG. 1 is a cross-sectional view of an apparatus for inhibiting blood loss in accordance with an embodiment of the present invention.

FIG. 1 illustrates an apparatus 10 for locating a puncture site in a blood vessel wall and for inhibiting blood loss from the puncture site according to the present invention. The apparatus 10 includes a tube 12, an elongated member 14, a dissolvable distal capsule 20, and sponge 26 located inside the dissolvable distal capsule 20. The elongated member 14 has a proximal end 16 and a distal end 18, and is positioned around the tube 12. In a preferred embodiment, the distal end 18 of the elongated member 14 has a substantially concave spherical shape. However, it can be appreciated that the distal end 18 of the elongated member 14 can have any concave shape including a rectangular, a stepped or a flat surface which accommodates the sponge 26 located inside the dissolvable distal capsule 20. At the distal end 18 of the elongated member 14, the elongated member 14 has a contact zone 34 in which the elongated member 14 has an outer diameter which is slightly smaller than the outer diameter of the more proximal portion of the elongated member 14 to allow the dissolvable distal capsule 20 to slide onto the contact zone 34 of the elongated member 14. In the preferred embodiment, the outer diameter of the elongated member 14 in the contact zone 34 is equal to the inner diameter of the dissolvable distal capsule 20, and the outer diameter of the distal capsule 20 is equal to the outer diameter of the elongated member proximal to the contact zone 34 to provide a smooth transition from the dissolvable distal capsule 20 to the elongated member 14. The outer diameter of the elongated member 14 proximal to the contact zone 34 is slightly larger than the access sheath or device that occupied the vessel puncture, and preferable 2 Fr larger.

Figure 3:
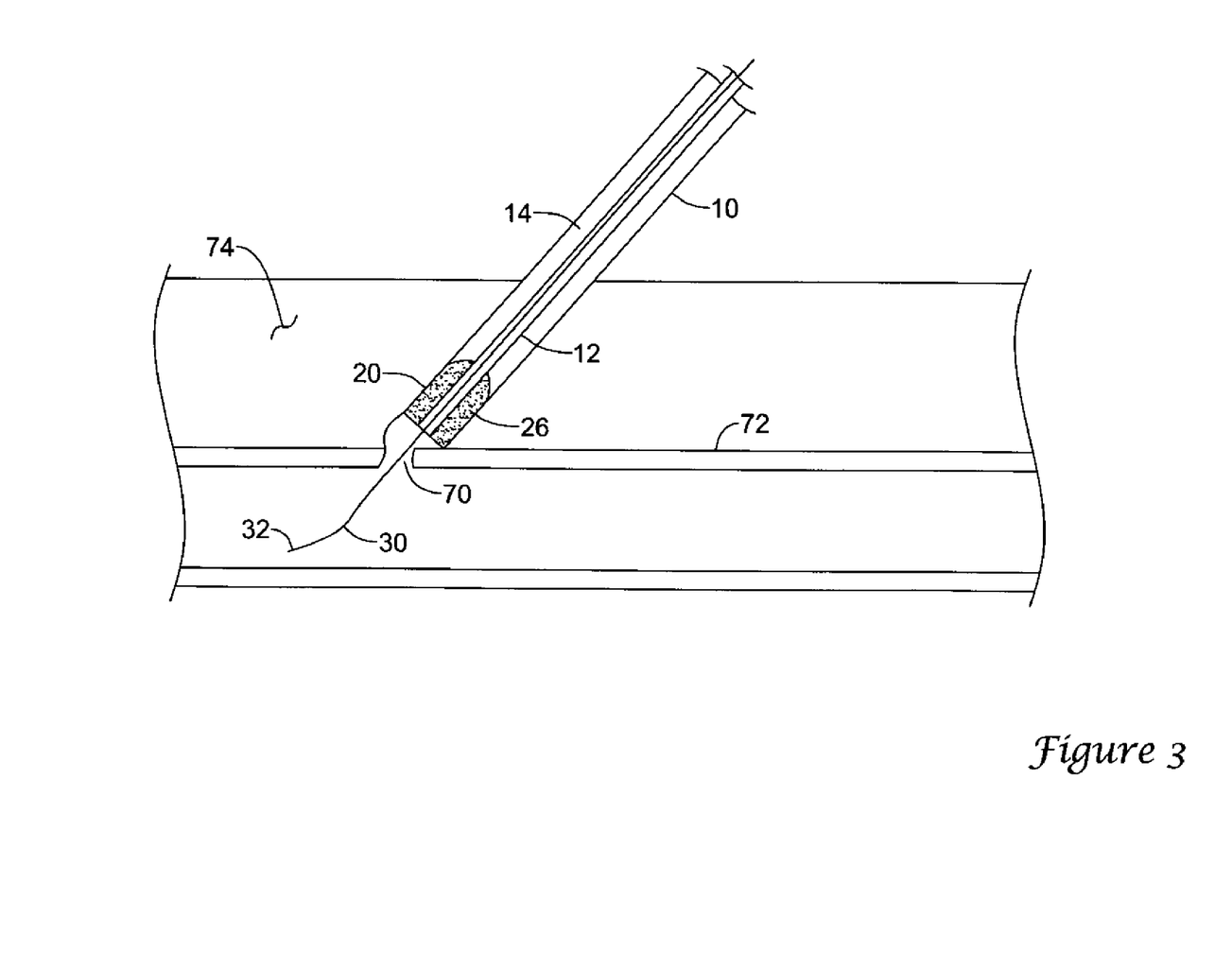
FIG. 3 is a cross-sectional view of a punctured blood vessel and an apparatus for inhibiting blood loss from a puncture site in accordance with the present invention.

The tube 12 has a proximal end 22 and a distal end 24 and extends longitudinally from the proximal end 16 beyond the distal end 18 of the elongated member 14. The tube 12 has an inner diameter of about 0.040 to 0.120 inches, preferably about 0.050 to 0.090 inches, and should loosely accommodate a guidewire 30, as shown in FIG. 3. The tube 12 has a wall thickness of about 0.0005 to 0.005 inches and preferably 0.001 to 0.002 inches. At the distal end 24 of the tube 12, the inner diameter 62 of the tube 12 is slightly greater than the inner diameter 60 of the tube 12 along its proximal portion to accommodate a cylindrical section 80 of the dissolvable distal capsule 20. In a preferred embodiment, the inner diameter 60 of the tube 12 is equal to the inner diameter 64 of the edge of the dissolvable distal capsule 20. For reasons that will be appreciated by those skilled in the art, the tube 12 can optionally be coated or otherwise protected with a material which inhibits blood coagulation. By way of example and not of limitation, the tube 12 can be coated with material including heparin (e.g. heparinized), tPa, or other functionally similar materials or compounds which inhibit or prevent blood from clotting or otherwise coagulating in the tube 12.

Figure 1A:
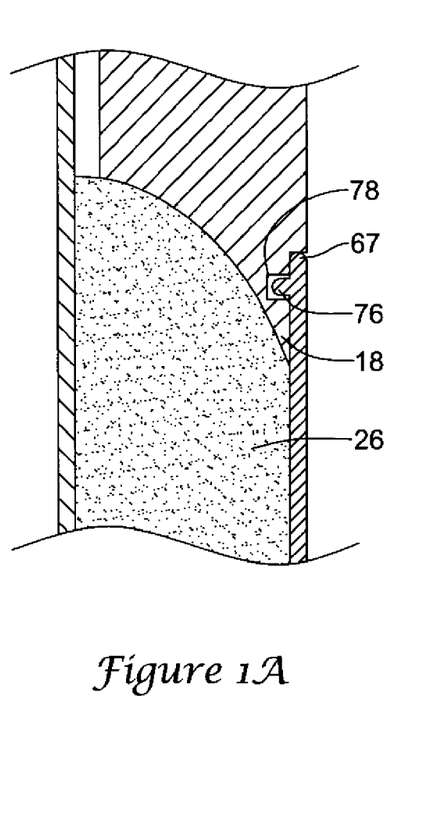
FIG. 1a is a section of the embodiment shown in FIG. 1.

The dissolvable distal capsule 20 is positioned around the tube 12, and has a proximal end 67 and a distal end 68. The dissolvable distal capsule 20 and the tube 12 form a coaxial space 66 therebetween for the sponge 26. The proximal end 67 of the dissolvable distal capsule 20 fits snugly around the distal end 18 of the elongated member 14 and can be attached thereto by adhesive or gelatin solution, or by wetting the capsule so that it becomes sticky prior to positioning the capsule 20 around the tube so that the capsule and the tube are bonded to one another. Alternatively, the capsule 20 can be held to the elongated member 14 by frictional engagement or by an interlock system such as an annular ring 76 formed in the capsule 20 and a corresponding annular groove 78 formed in the elongated member 14, as shown in FIG. 1a.

The dissolvable distal capsule 20 includes an outer tubular section having a proximal end 67 and a distal end 68. The proximal end 67 is open, having an inner diameter slightly greater than or equal to the outer diameter 36 of the elongated member 14 at the elongated member's distal end 18. The distal end 68 of the dissolvable distal capsule 20 is rounded to prevent catching on subcutaneous tissue as the apparatus 10 is inserted through the epidermal outer layer and subcutaneous tissue. The distal end of the capsule 20 has cylindrical section 80 for receiving the tube 12. The cylindrical section 80 has a proximal end 82 and a distal end 84, and the outer diameter of the cylindrical section 80 is approximately equal to or slightly smaller than the inner diameter of the tube 12.

The elongated member 14 is preferably a rigid or semi-rigid polymer such as PVC (polyvinyl chloride) or polycarbonate, but may be made of any suitable material, including SST. The tube 12 can be made from any number of polymers or from thin wall SST. The dissolvable distal capsule 20 is made from known absorbable, biocompatible materials, such as gelatin films like Gelfilm® from Upjohn, similar gel-cap vitamins, gelatin and sugar, gelatin and glycerin, sugar, PGA, or other similar materials. Preferably we use gelatin film; preferably the hardness of the gelatin film forming the distal capsule is between about 40 and about 80 on the Shore A scale; and preferably it has a bloom of at least 270, which is normally called "high" bloom. However, in some circumstances the gelatin film could have a hardness and bloom outside these ranges. The sponge 26 is preferably a liquid permeable, water-soluble gelatin based sponge. Other hemostatic material can be used as well, instead of sponge 26, such as fibrillar collagen, collagen sponge, regenerated oxidized cellulose, gelatin powder, or hydrogel particles. Alternatively, the sponge may be composed of an absorbable collagen or other types of absorbable polymers. One type of absorbable sponge material which is acceptable for use in the present invention is Gelfoam™, manufactured by the Pharmacia & Upjohn Company. Gelfoam™ is a porous, pliable, cross-linked gelatin material and is available commercially in sheet form as pre-compressed or non-compressed sponge. Alternatively, the sponge can be made by mixing a suitable organic solvent (e.g., formaldehyde) with an aqueous solution of gelatin. The organic solvent facilitates the cross linkage of gelatin polymers. It is expected that glutaraldehyde may also be suitable. The resulting solution is then incubated typically at slightly above room temperature (30.degree.-40. degree. C.). Thereafter, the solution is aerated to cause it to foam, and the foam is dried to produce the absorbable sponge material.

Suitable absorbable sponge materials are described in U.S. Pat. No. 2,465,357 which is incorporated herein by reference.

The apparatus 10 may be assembled by placing the tube 12 within the dissolvable distal capsule 20, then compressing the sponge 26 and placing it within the coaxial space 66 between the tube 12 and dissolvable distal capsule 20. The sponge can be compressed to between 90% and 5% of its uncompressed cross-sectional thickness. The elongated member 14 is then placed over the proximal end 22 of the tube 12 and inserted into the dissolvable distal capsule 20 and can be used to apply pressure to further compress the sponge, if desired.

Figure 2:
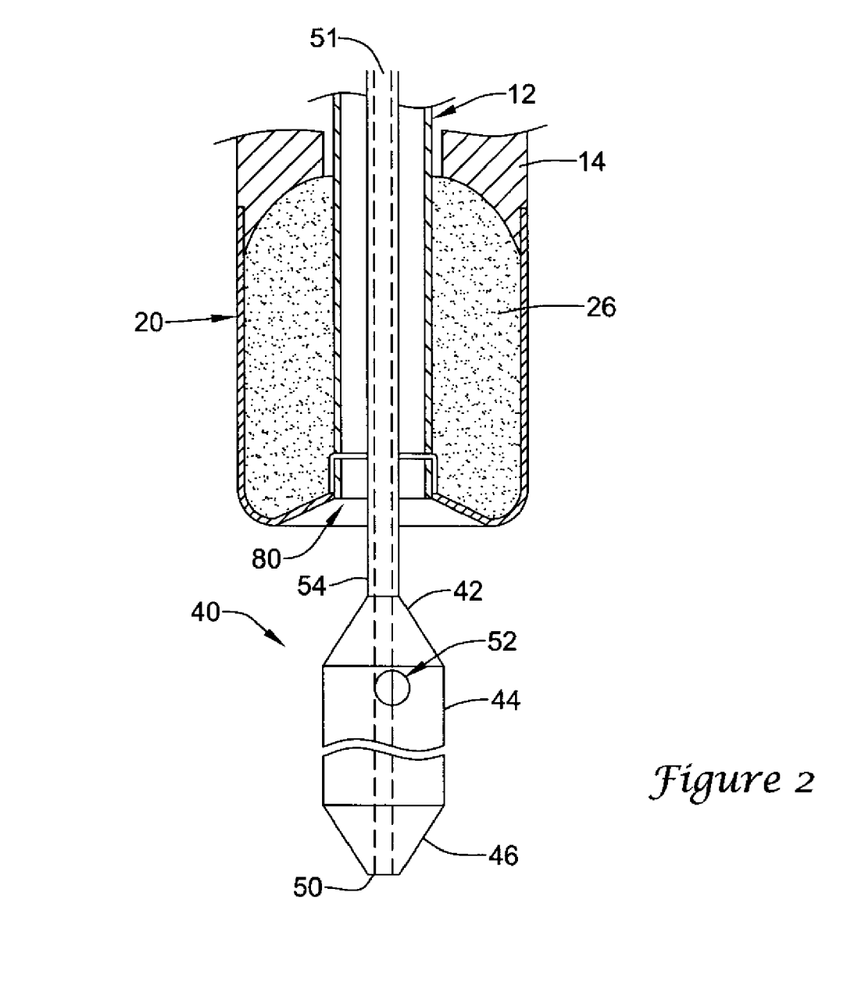
FIG. 2 is a cross-sectional view of an apparatus for inhibiting blood loss from a puncture site with a control tip assembly in accordance with an embodiment of the present invention.

FIG. 2 illustrates an alternative embodiment of apparatus 10 of FIG. 1 further including a control tip assembly 40. The control tip assembly 40 at its proximal end is mounted to a tube 54. The control tip assembly 40 includes a proximal end portion 42, a distal end 46 portion having a distal port 50, and a central portion 44 between the proximal end portion 42 and the distal end portion 46. The control tip assembly 40 includes a lumen 51 that extends longitudinally between proximal end portion 42 and the distal end portion 46. The lumen also extends through tube 54. For reasons that will be readily appreciated by one of ordinary skill in the art, the lumen 51 can optionally be coated or otherwise provided with an interior surface which inhibits blood coagulation. Further, by way of example and not of limitation, the lumen 51 can be coated with material including heparin (e.g. heparinized), tPa, or other functionally similar materials or compounds which inhibit or prevent blood from clotting or otherwise coagulating in the lumen 51.

As illustrated in FIG. 2, the center portion 44 preferably has a constant outer diameter. The proximal and distal ends are tapered; however, it can be appreciated that the proximal and distal end portions 42 and 46 can alternatively be a step, rounded shoulder, or the like. The control tip assembly 40 also includes a hole 52 that connects the exterior of the control tip assembly 40 with the lumen 51. The lumen 51 has an inner diameter selected to be larger than the external diameter of a guidewire, preferably an exchange wire, used therewith. Furthermore, a plurality of holes (not illustrated) can be formed in the control head, circumferentially spaced and at the same longitudinal location as hole 52.

The proximal and distal portions 42, 46 of the control tip assembly 40 can be relatively thin walled such that the internal dimensions of the lumen 51 in the central portion 44 is larger than in the proximal end portion 42 and distal portion 46 of the control tip assembly 40. As also described briefly above, the distal portion 46 of control tip assembly 40 includes a distal port 50 having an internal opening diameter also selected to be larger, and preferably only slightly larger, than the external diameter of the guidewire 30 used with the control tip assembly. While the function of the distal port 50 in conjunction with a guidewire 30 will be described in greater detail below, one aspect of the present invention is that by selecting the external diameter of guidewire 30 and the inner diameter of the distal port 50 to be only slightly different, blood flow into interior of control tip assembly 40 is greatly restricted, thus allowing the hole 52 to be the sole entrance into the control tip for blood to flow up the lumen 51 to indicate that the control tip assembly 40 has been located in a blood vessel.

Preferably, the control tip assembly is formed of a flexible, biocompatible material, such as a thermoplastic. By way of example and not of limitation, the material out of which the control tip is formed has a Shore hardness between about 98A-74D.

For the control tip assembly herein, the outer diameter of the central portion 44 is between about 4 French and about 10 French, preferably between about 6 French and about 8 French. It is preferably equal to or similar in diameter to the access sheath that was used to make the puncture. The length of the control tip assembly, between the distal most end and the proximal end of the proximal end portion 42, should be at least about 1 inch and preferably about 8 inches (6.4 cm), and more preferably about 2 to 4 inches. Control tip assemblies of these dimensions are well suited for controlling puncture sites as described herein, particularly puncture sites used during percutaneous-type vascular access.

FIG. 3 illustrates the operation of the apparatus 10 as shown in FIG. 1. After an endoluminal procedure which has been performed using, in part, a percutaneous access sheath for access to the patient's vasculature, a guidewire 30 is advanced through the sheath, into the patient's blood vessel 72 through a puncture site 70 in the vessel wall, and the sheath is removed. The apparatus 10 is then placed over the guide wire 30 and pushed through the patient's skin. The operator uses the apparatus 10 to locate the desired delivery location by bumping into the artery 72. Once the desired delivery position is achieved, the operator retracts the tube 12 to expose at least part of the sponge 26 to blood from blood vessel 72, which starts the process of sponge expansion. Simultaneously, the dissolvable distal capsule 20 is exposed to blood and begins to soften and dissolve. The dissolvable distal capsule 20 dissolves in about 30 sec. to 10 min. and preferably in about 1 minute. Once the dissolvable distal capsule has dissolved, the sponge 26 is free to expand into the puncture site. The dissolvable distal capsule 20 will also release itself from the elongated member body 14 as a result of softening and dissolving of the capsule. During and after dissolution of the capsule the operator may apply pressure over the site. Then the operator can then apply diffuse external pressure to the tissue over the sponge 26 and remove the guidewire 30 and the elongated member 14.

Figure 4:
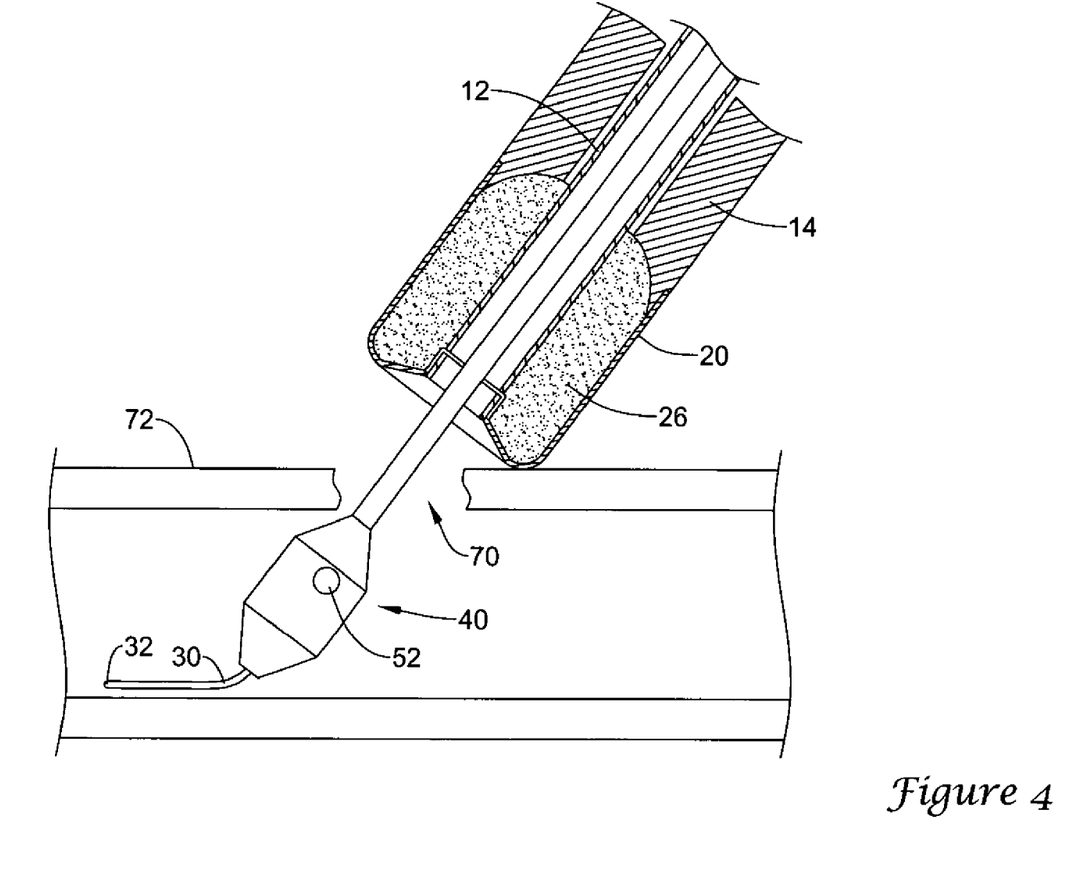
FIG. 4 is a cross-sectional view of a punctured blood vessel and an apparatus for inhibiting blood loss from a puncture site with a control tip assembly (as shown in FIG. 2) in accordance with the present invention.

The use of the FIG. 2 embodiment of apparatus 10 is shown in FIG. 4. The operator places the control tip assembly 40 over the proximal end of the guidewire 30 which extends from the patient's artery and pushes the apparatus through the patient's skin. The apparatus 10 locates the desired location by bumping into the arterial puncture site 70. The control tip assembly 40 provides additional benefits such as hemostasis and bleedback via the bleedback hole 52 or through the tube 54. Once in the desired delivery location, the tube 12 is retracted to expose the sponge 26 from the puncture site 70 and the blood vessel 72. This starts the process of sponge 26 expansion. When the user observes that the bleedback of the tube 54 is diminishing significantly, the control tip assembly 40 can be retracted far enough to control the puncture site 70. As discussed above in connection with FIG. 3, the dissolvable distal capsule 20 softens and dissolves, releasing the sponge 26 into the puncture site and detaching the sponge 26 from the elongated member 14. The control tip assembly 40 is then completely removed from the puncture site 70 and the skin 74. During and after dissolution of the capsule the operator may apply pressure over the site. The operator then applies diffuse external pressure to the tissue over the sponge 26 and removes the guidewire, elongated member 14 and tube 12, if it has not already been removed.

Figure 5:
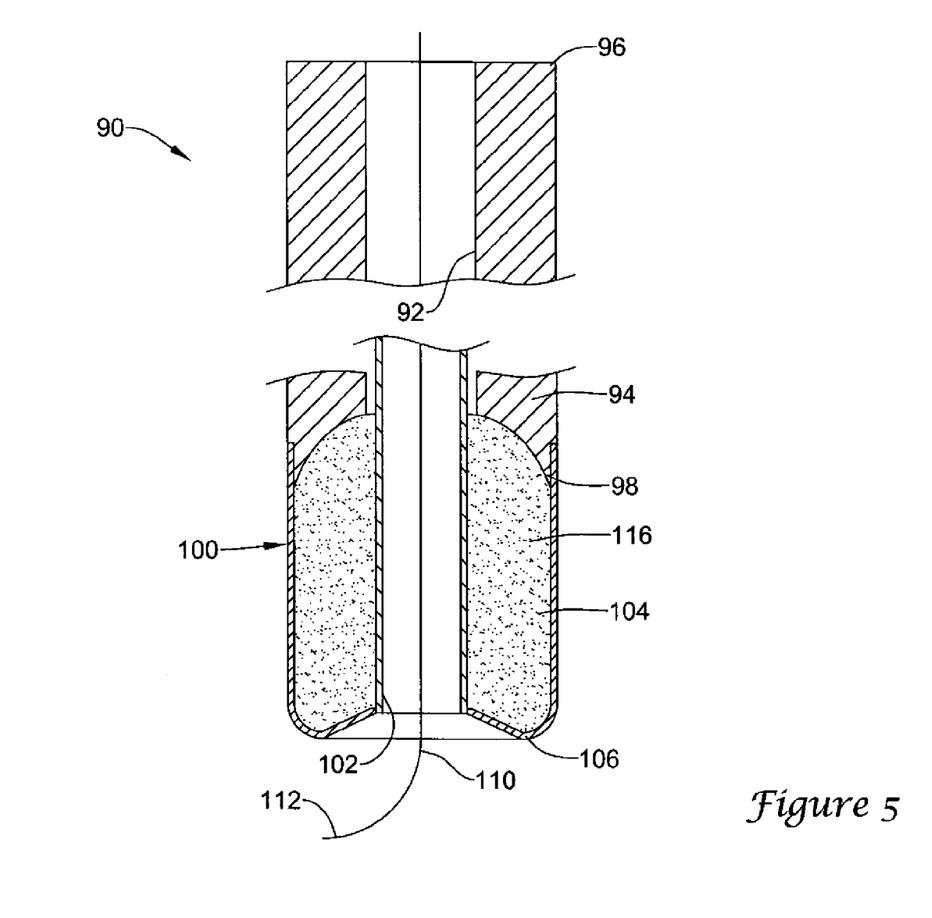
FIG. 5 is a cross-sectional view of an apparatus for inhibiting blood loss in accordance with another embodiment of the present invention.

In an alternative embodiment illustrated in FIG. 5, the tube 12 shown in FIG. 1 is eliminated. The apparatus 90 includes an elongated member 94 having a lumen 92 for receiving a guidewire 110, a dissolvable distal capsule 100 positioned around the lumen 92 and a sponge 116 located inside the dissolvable distal capsule 100. The lumen 92 (which is defined by the inner surface of the elongated member 94) for receiving the guidewire 110 extends from a proximal end 96 of the elongated member 94 to a distal end 98 of the elongated member 94. A dissolvable distal capsule 100 attaches to the distal end 98 of the elongated member 94 as described above. In this embodiment the dissolvable capsule includes an inner cylindrical portion 102 that extends approximately the same length as the outer cylindrical portion 104 and into at least a portion of the elongated member 94. The capsule has a rounded end 106 extending between the inner cylindrical portion 102 and the outer cylindrical portion 104.

In operation, the apparatus 90 as shown in FIG. 5 is placed over the proximal end 112 of a guidewire 110 extending from a patient's artery and the apparatus 90 is advanced into the patient. The apparatus 90 locates the desired delivery location by bumping into the arterial puncture site to obtain the desired delivery position. This starts the process of sponge 116 expansion, wherein the dissolvable distal capsule 100 begins to soften and dissolve rapidly. Once the dissolvable distal capsule 100 has dissolved, the sponge 116 is free to expand into the puncture site and secure itself within the puncture site. The dissolvable distal capsule 100 will also release itself from the elongated member 94 body as a result of softening and dissolving of the dissolvable distal capsule 100.

Figure 6:
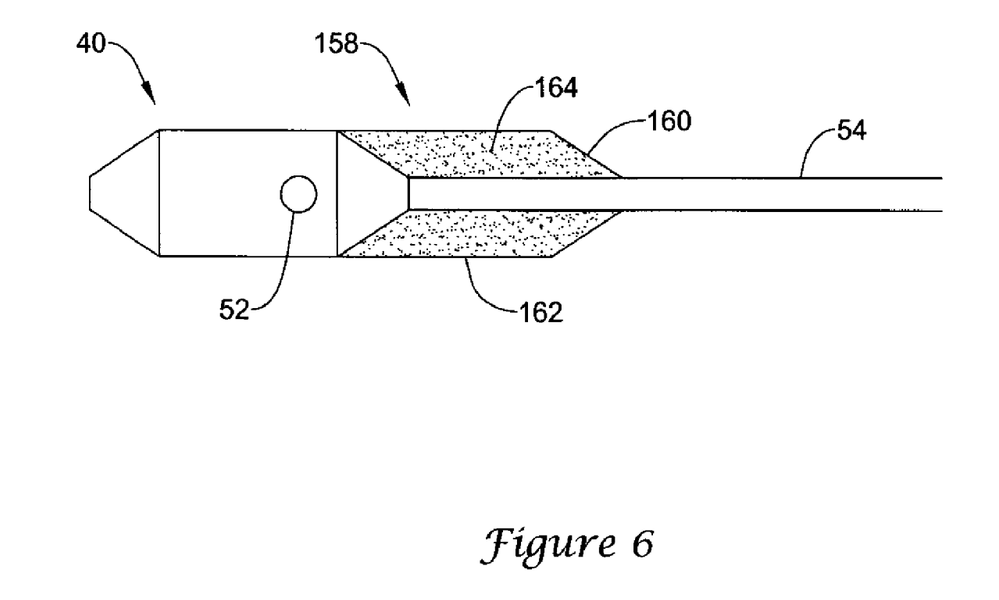
FIG. 6 is yet another embodiment of a device according to the present invention.

FIG. 6 illustrates another embodiment. This embodiment includes a control tip assembly 40 as shown in FIG. 2 and described above. A proximal gelatin capsule 158 is connected to the control tip 40 assembly proximally thereof. The proximal gelatin capsule 158 consists of a truncated cone-shaped portion 160 and a cylindrical portion 162 connected to the distal end of the cone-shaped portion, both of which are constructed of the same material as the dissolvable distal capsule 20, e.g. gelatin. Located within the proximal gelatin capsule 158 is a compressed sponge 164 which is formed of the same material as sponge 26. The proximal gelatin capsule 158 includes cylindrical openings at each end to fit snugly over the control tip 40 and snugly over the tube 54 so when an operator pushes the device through a patient's skin there is minimal frictional resistance between the leading edge of the proximal gelatin capsule 158 and the skin. Furthermore, the compressed sponge 164 can be packed tightly against the tube 54 and control tip assembly 40 to provide friction therebetween so that that proximal gelatin capsule 158 remains in place when the operator pushes the device through the patient's skin. Alternatively, the control tip assembly 40 and proximal gelatin capsule 158 may be inserted through a procedural access sheath which is already in place.

In use, the portion of the tube 54 extending proximally of the proximal gelatin capsule 158 may have a diameter smaller than the control tip 40 or equal to the control tip 40. If the tube 54 is smaller than the control tip 40 and the control tip outside diameter is equal to or slightly smaller than the inside diameter of the access sheath 182, the capsule may be positioned as shown in FIG. 14b. Starting with the sheath already extending into a vessel 72, the assembly 188 is pushed in through the sheath 182 until the cylindrical portion 162 extends distally of the distal end 190 of the sheath 182 and bleed back indication is observed via blood entering the distal end 190 of the sheath. The assembly 188 and sheath 182 are then withdrawn as one until bleed back indication first stops. The sheath 182 and assembly 188 are then withdrawn an "additional distance" to properly position the hemostatic material.

Figure 7A:
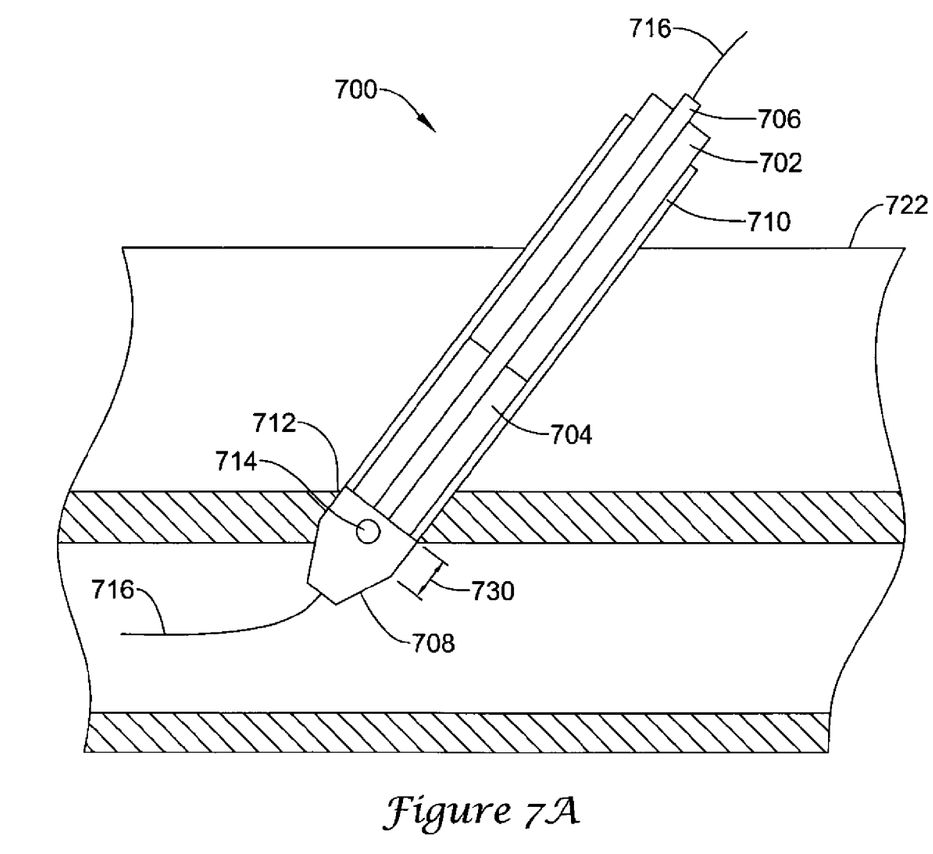
FIGS. 7A and 7B illustrate a dissolvable closure device in accordance with an embodiment of the present invention.
Figure 7B:
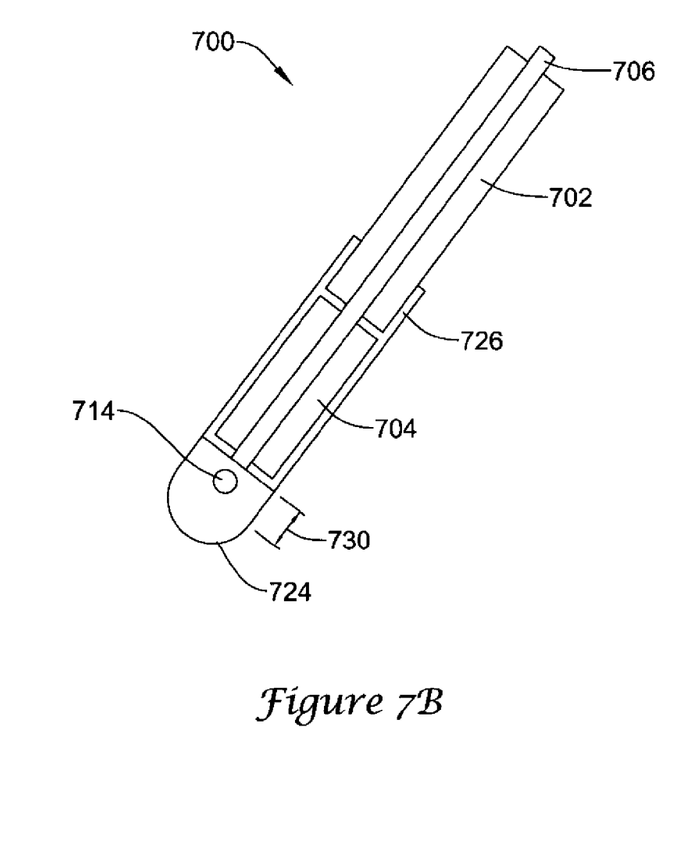

FIGS. 7A and 7B illustrates the dissolvable closure device in accordance with an embodiment of the present invention. FIG. 7A illustrates the dissolvable closure device 700 having a dissolvable distal tip 708, a communication tube 706 attached to the dissolvable distal tip 708, the communication tube 706 having a lumen 732, a top 736 and a bottom 734. A sponge 704 surrounds the communication tube bottom 734 adjacent the dissolvable distal tip 708. A sponge cover 710 is positioned around the sponge 704 and placement tube 702. The dissolvable closure device 700 is shown with the sponge 704 located at the blood vessel puncture site 712. As further discussed below, all or parts of the device 700 may be made of any of the dissolvable materials as disclosed above.

The dissolvable distal tip 708 may include a bleed back entrance port 714 that is in fluid communication with the communication tube 706. Blood entering the bleed back entrance port 714 may bypass the sponge and be observed by a user out of a bleed back exit port (not shown) at the proximal end 718 of the device. The dissolvable distal tip 708 and sponge 704 may include clot accelerators as discussed above. As shown in FIG. 7B, the dissolvable distal tip 724 may be any shape such as the hemisphere as shown in FIG. 7B, a conical taper as shown in FIG. 7A, hyperbolic cone, concave, or similar other shapes.

The sponge cover 710 is an outer covering for the sponge 704 to protect and prevent the sponge 704 from expanding prior to a user positioning the device 700. The sponge cover 710 may extend the entire length of the device 700 and out of the skin 722 as shown in FIG. 7A. However, the sponge cover 726 may only cover the sponge 704 as shown in FIG. 7B and be positioned similarly as described above with reference to FIGS. 1 and 1a to provide stability during advancement of the device 700 into the blood vessel lumen 720. In this embodiment, the sponge cover is preferably made of an absorbable material.

The placement tube 702 may reside proximally of the sponge and extend proximally far enough to exit the skin 722. However, the placement tube 702 need not extend out of the skin 722 if made of an absorbable material. The sponge 704 may be fixed together with the placement tube 702 or the device 700 may be used without the placement tube 702 similar to FIG. 5 described above. If the sponge cover 710 or 726 is made of an absorbable material, it is preferable that the sponge cover 710 or 726 be adhered to or frictionally fixed to the sponge 704 or distal tip 708 or 724. Additionally, the sponge cover 710 may comprise perforations to accelerate blood infiltration into the sponge.

A guidewire 716 may be received through the communication tube 706. However, the use of a guidewire 716 may not be necessary. Additionally, an access sheath (not shown) commonly used in surgical procedures may be used to position the device through the tissue tract and into the blood vessel lumen. However, the use of the access sheath may also not be necessary.

In use, the dissolvable closure device 700 is positioned within the blood vessel lumen 720 until blood enters the bleed back entrance port 714. When the user observes bleed back out of the bleed back exit port, the user may then withdraw the device 700 until bleed back is no longer observed. The device 700 may then be accurately positioned at the blood vessel puncture site 712.

The use of device 700 may vary as illustrated in Examples 1 and 2 below:

Example 1

The dissolvable tip 708 or 724, sponge 704, and sponge cover 710 are made of an absorbable material. The communication tube 706 and placement tube 702 are made of non-absorbable materials. Once positioned, the communication tube 706, placement tube 702, and guidewire 716 are removed while the sponge cover 710 is held stationary. As discussed in connection with FIG. 3, the dissolvable distal tip 708 and sponge cover 710 may soften and dissolve. This starts the process of sponge 704 expansion which may be positioned within the puncture site 712 as shown in FIG. 7A or may be positioned outside the puncture site 712 (not shown). The sponge cover 710 may then be cut off (not shown) below the skin 722 or left to dissolve if the sponge cover 710 extends outside the skin 722. The remainders of the sponge cover 710 above the skin 722 may be released once the sponge cover 710 is dissolved below the skin 722.

Example 2

The dissolvable tip 702 or 724, communication tube 702, and sponge 704 are made of an absorbable material. The sponge cover 710 and placement tube are made of non-absorbable materials. Once positioned, the sponge cover 710 of FIG. 7A is removed while the placement tube 702 is held stationary. If the sponge cover 726 of FIG. 7B is used, it does not need to be removed. The placement tube 702 and guidewire 716 are then removed while the communication tube 702 is held stationary. This starts the process of sponge 704 expansion. As discussed above in connection with FIG. 3, the dissolvable distal tip 708 may soften and dissolve. The sponge 704 may then be positioned within the puncture site 712 or may be positioned outside the puncture site 712 (not shown). If required, the user may reposition the device 700 using the communication tube 702 at any time. The communication tube 702 may be cut off below the skin 722 or left in place to dissolve. The remainders of the communication tube 702 above the skin 722 may be released once the communication tube 702 is dissolved below the skin 722.

During and after dissolution of the sponge 704 in either examples above, the operator may apply pressure over the blood vessel puncture site 712. The operator may then apply diffuse external pressure to the tissue over the sponge 704. The Examples are merely for illustration purposes and are not meant to limit the present invention.

Figure 8:
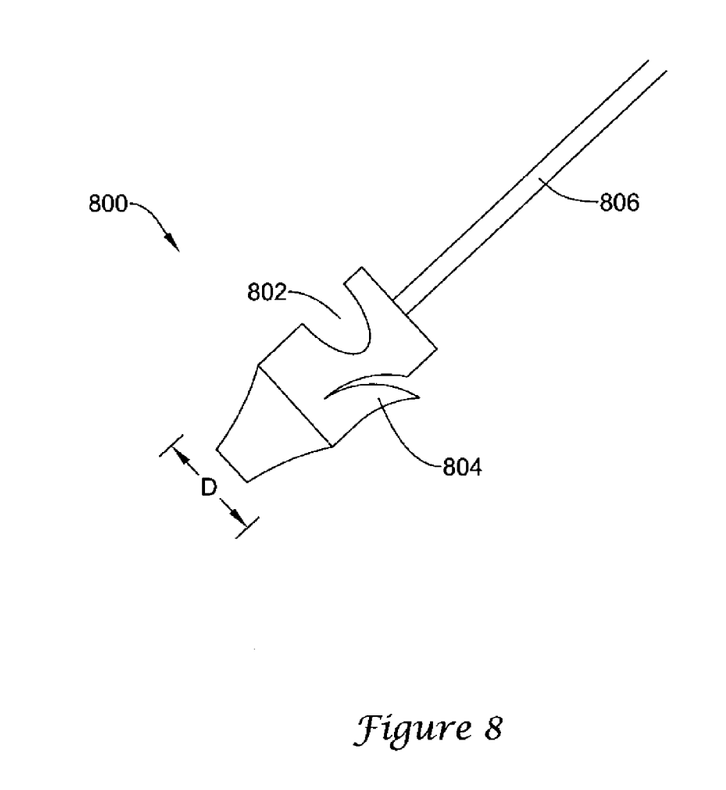
FIG. 8 illustrates an embodiment of a dissolvable distal tip of the present invention.

FIG. 8 is an illustration of a dissolvable tip for use with the dissolvable closure device of the present invention. The dissolvable tip 800 has a diameter D, a bleed back entrance port 802 having a diameter greater than or equal to 50% of diameter D, and a finger 804. Additional details of bleed back entrance port 802 and finger 804 are discussed further in co-pending patent application Ser. No. 10/462,065 which is incorporated herein by reference and will not be discussed in the present application. The bleed back entrance port 802 is in fluid communication with a communication tube 806. The dissolvable tip 800 and communication tube 806 are attached and are preferably made of an absorbable material and may be used as similarly described in Example 2 above.

Figure 9:
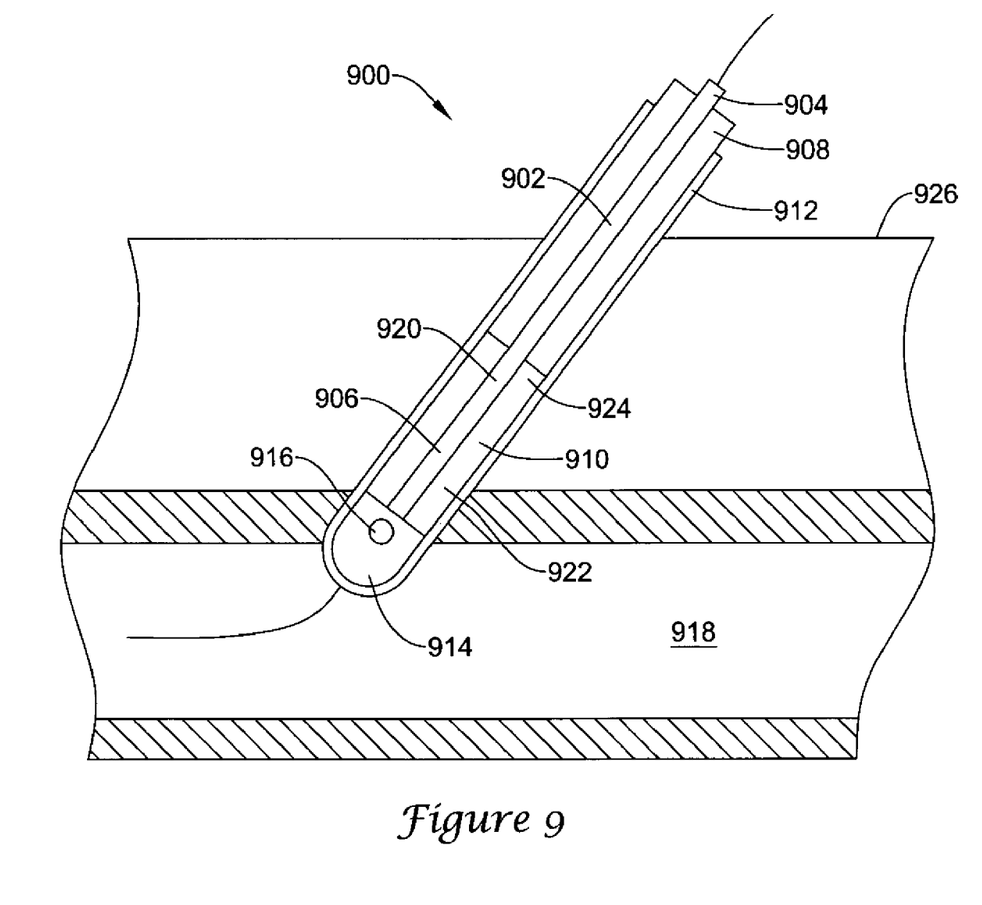
FIG. 9 illustrates a dissolvable closure device in accordance with another embodiment of the present invention.

FIG. 9 is an illustration of the dissolvable closure device in accordance with another embodiment of the present invention. The device 900 has a communication tube 902 having a lumen 920, a top 904 and a bottom 906. A sponge 910 is positioned around the communication tube bottom 906, having a first end 922 and a second end 924. A sponge cover 912 is positioned around the sponge 910 and communication tube bottom 906 thereby forming a hollow distal tip cavity 914 at the sponge first end 922. FIG. 9 is illustrated with the use of a placement tube 908, however, the device 900 may be used without the placement tube 908 similar to FIG. 5 described above.

The sponge may be adhered to or frictionally fixed to the communication tube 902 and sponge cover 912 with gelatin, an absorbable adhesive, or any other materials as discussed above. Additionally, the sponge cover 912 may comprise perforations to accelerate blood infiltration into the sponge. Furthermore, the sponge cover may be similar in shape to the covers described in co-pending U.S. patent application Ser. No. 10/460,859 filed Jun. 12, 2003, by inventors Mark Ashby and Tin Tran, entitled "Hemostatic Device Including A Capsule", which is herein incorporated by reference in its entirety.

The hollow distal tip cavity 914 and sponge 704 may include clot accelerators as discussed above. The hollow distal tip cavity 914 may be any shape such as the hemisphere as shown in FIG. 9, a conical taper as shown in FIG. 7A, hyperbolic cone, concave, or similar other shapes. Furthermore, the hollow distal tip cavity 914 may include the bleed back entrance hole 916 as shown in FIG. 9 or the bleed back entrance hole 802 as shown in FIG. 8. Additionally, the hollow distal tip cavity 914 may comprise the finger 804 as illustrated in FIG. 8.

The dissolvable closure device 900 may extend beyond the patient's skin 926, or extend below the skin 926. In use, the device 900 may be used similarly as described in Example 1 and 2 above.

A guidewire 914 may be used and may be positioned through the communication tube 910. However, the use of a guidewire 914 may not be necessary. Additionally, an access sheath (not shown) commonly used in surgical procedures may be used to position the device through the tissue tract and into the blood vessel lumen. However, the use of the access sheath may not be necessary.

Sponges used in the present invention may be about 1 cm-4 cm in length and preferably 1 cm-2 cm in length. The sponge material should be chosen to absorb quickly, within 30 seconds to one hour. However, longer absorption times, such as within 90 days or more, will also be possible if desired. However, the longer absorption times may limit re-access to the puncture site, if re-access is necessary. Furthermore, it may be beneficial if the sponge covering, dissolvable distal tip, communication tube, and placement tube dissolve (if made of an absorbable material) quickly enough to release the sponge within 30 seconds to 5 minutes. However, longer dissolution times may be used if desired.

The diameter of device 700, 800 or 900 may be about 2 F-25 F, and preferably 4 F-20 F. However, the diameter may be equal to the inner diameter of an access sheath, if used. It will further be appreciated that the diameter may be equal to the outer diameter of an access sheath, if the access sheath is not used, to provide for proper blood control of the puncture site.

It is important that the dissolvable tip and sponge of the above embodiments remain stationary after proper placement of the device. It is appreciated that the embodiments of the dissolvable distal tip, such as the finger 804 and bleed back entrance port 802 are provided to assist in retention of the device, rather than to hold the dissolvable tip and sponge in proper position.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. An apparatus to provide hemostasis at a puncture site, comprising:
   a communication tube having a lumen, a top and a bottom, further comprising a guidewire received within said communication tube lumen;
   a hemostatic material positioned around said communication tube bottom, said hemostatic material having a first end and a second end; and
   a hemostatic material cover positioned around the hemostatic material and said communication tube bottom, wherein said hemostatic material cover forms a hollow distal tip cavity at the hemostatic material first end;

wherein the distal tip, the hemostatic material, and the hemostatic material cover are made of an absorbable material.

2. The apparatus of claim 1 wherein said hollow distal tip cavity further comprises a bleed back entrance port in fluid communication with said communication tube.

3. The apparatus of claim 2 wherein said bleed black entrance port has a diameter equal to or greater than a distal tip diameter.

4. The apparatus of claim 3 wherein said hollow distal tip cavity further comprises a finger positioned adjacent said bleed back entrance port.

5. The apparatus of claim 1 further comprising a placement tube positioned around said communication tube wherein said placement tube is adjacent said hemostatic material second end.

6. The apparatus of claim 5 wherein said hemostatic material cover is positioned around said placement tube.

7. The apparatus of claim 5 wherein said placement tube is made of an absorbable material.

8. The apparatus of claim 1 wherein said hollow distal tip cavity further comprises a finger positioned adjacent said hemostatic material first end.

9. The apparatus of claim 1 wherein said communication tube is made of an absorbable material.

10. An apparatus for promoting hemostasis at a puncture site, comprising:
   means for inserting a hemostasis device over a guidewire into said puncture site using a placement tube, said hemostasis device having a hemostasis material cover;
   means for visualizing a blood flow out of a communication tube at least partially surrounded by a hemostatic material, said communication tube in fluid communication with a bleed back entrance port;
   means for withdrawing said hemostasis device until said blood flow slows or stops;
   means for removing said communication tube and said placement tube; and
   means for allowing said hemostasis material cover to dissolve at least partially.

11. The apparatus of claim 10 wherein said means for removing further comprises means for holding said hemostasis material cover stationary.

12. An apparatus for promoting hemostasis at a puncture site, comprising:
   means for inserting a hemostasis device into said puncture site using a placement tube, said hemostasis device having a hemostasis material cover, and wherein said means for inserting further comprises means for inserting said hemostasis device over a guidewire;
   means for removing said guidewire;
   means for visualizing a blood flow out of a communication tube, said communication tube in fluid communication with a bleed back entrance port;
   means for withdrawing said hemostasis device until said blood flow slows or stops;
   means for removing said communication tube and said placement tube; and
   means for allowing said hemostasis material cover to dissolve at least partially.

13. An apparatus for promoting hemostasis at a puncture site, comprising:
   means for inserting a hemostasis device into said puncture site using a placement tube, said hemostasis device having a hemostasis material cover;
   means for visualizing a blood flow out of a communication tube, said communication tube in fluid communication with a bleed back entrance port;
   means for withdrawing said hemostasis device until said blood flow slows or stops;
   means for removing said communication tube and said placement tube;
   means for allowing said hemostasis material cover to dissolve at least partially; and
   means for cutting said hemostasis material cover at a patient's skin.

14. An apparatus to provide hemostasis at a puncture site, comprising:
   a distal tip;
   a communication tube attached to the distal tip having a lumen, a top and a bottom;
   a guidewire received within said communication tube lumen;
   a hemostatic material positioned around said communication tube bottom adjacent said distal tip; and
   a hemostatic material cover positioned around the hemostatic material;
   wherein the distal tip, the hemostatic material, and the hemostatic material cover are made of an absorbable material.

15. The apparatus of claim 14 wherein said distal tip further comprises a bleed back entrance port in fluid communication with said communication tube.

16. The apparatus of claim 15 wherein said bleed back entrance port has a diameter equal to or greater than fifty percent of a distal tip diameter.

17. The apparatus of claim 16 wherein said distal tip further comprises a finger positioned adjacent said bleed back entrance port.

18. The apparatus of claim 14 further comprising a placement tube positioned around said communication tube top wherein said placement tube is adjacent said hemostatic material.

19. The apparatus of claim 18 wherein said hemostatic material cover is positioned around said placement tube.

20. The apparatus of claim 18 wherein said placement tube is made of an absorbable material.

21. The apparatus of claim 14 wherein said distal tip further comprises a finger positioned adjacent said hemostatic material.

22. The apparatus of claim 14 wherein said communication tube is made of an absorbable material.

23. An apparatus for promoting hemostasis at a puncture site comprising:
   means for inserting a hemostasis device into said puncture site using a placement tube and guidewire;
   means for visualizing a blood flow out of a communication tube at least partially surrounded by a hemostatic material;
   means for withdrawing said hemostasis device until said blood flow slows or stops;
   means for removing said placement tube while holding said communication tube stationary; and
   means for allowing said hemostasis device to dissolve at least partially.

24. The apparatus of claim 23 wherein said hemostasis device is made of an absorbable material.

25. An apparatus for promoting hemostasis at a puncture site, comprising:
   means for inserting a hemostasis device into said puncture site using a placement tube, and wherein said means for insetting further comprises means for insetting said hemostasis device over a guidewire;

means for visualizing a blood flow out of a communication tube;

means for withdrawing said hemostasis device until said blood flow slows or stops;

means for removing said placement tube while holding said communication tube stationary; and means for allowing said hemostasis device to dissolve at least partially.

26. The apparatus of claim 25 wherein said means for removing further comprises means for removing said guidewire.

27. An apparatus for promoting hemostasis at a puncture site, comprising:

means for inserting a hemostasis device into said puncture site using a placement tube and a guide member;

means for visualizing a blood flow out of a communication tube;

means for withdrawing said hemostasis device until said blood flow slows or stops;

means for removing said placement tube while holding said communication tube stationary;

means for allowing said hemostasis device to dissolve at least partially; and means for cutting said hemostasis device at a patient's skin.

* * * * *